United States Patent [19]
Ohtani et al.

[11] Patent Number: 5,132,404
[45] Date of Patent: Jul. 21, 1992

[54] METHOD OF PURIFYING HUMAN SERUM ALBUMIN USING ORGANIC CARBOXYLIC ACIDS AND ACETYL TRYPTOPHAN

[75] Inventors: Wataru Ohtani; Akinori Sumi; Takao Ohmura; Yahiro Uemura, all of Osaka, Japan

[73] Assignee: Green Cross Corporation, Osaka, Japan

[21] Appl. No.: 584,023

[22] Filed: Sep. 18, 1990

[30] Foreign Application Priority Data

Sep. 18, 1989 [JP] Japan .................. 1-239877

[51] Int. Cl.$^5$ .................. C07K 3/28; C07K 15/06; C12N 15/14
[52] U.S. Cl. .................. 530/364; 435/69.6; 435/71.1; 530/362; 530/363
[58] Field of Search .................. 530/363, 362, 364; 405/69.6, 71.1

[56] References Cited

U.S. PATENT DOCUMENTS

| | | | |
|---|---|---|---|
| 2,444,679 | 4/1954 | Fernandes et al. | 530/381 |
| 2,765,299 | 10/1956 | Porsche et al. | 530/364 |
| 3,100,737 | 8/1963 | Auerswald et al. | 530/364 |
| 3,992,367 | 11/1976 | Plan et al. | 530/364 |
| 4,177,188 | 12/1979 | Hansen | 530/364 |
| 4,426,323 | 1/1984 | Jain | 435/71.2 |
| 4,613,501 | 9/1986 | Horowitz | 424/89 |
| 4,675,387 | 6/1987 | Korant | 435/71.1 |
| 4,754,019 | 6/1988 | Gion et al. | 530/364 |
| 4,841,023 | 6/1989 | Horowitz | 530/364 X |
| 4,914,027 | 4/1990 | Knapp et al. | 435/69.6 |
| 4,939,176 | 7/1990 | Seng et al. | 530/363 |

FOREIGN PATENT DOCUMENTS

| | | |
|---|---|---|
| 0123544 | 4/1984 | European Pat. Off. . |
| 0248657 | 6/1987 | European Pat. Off. . |
| 0251744 | 6/1987 | European Pat. Off. . |
| 0248637 | 9/1987 | European Pat. Off. . |

OTHER PUBLICATIONS

Chemical Abstracts, vol. 98, No. 8, Feb. 21, 1983, p. 351, Abstract No. 59878u, Columbus, Ohio, US; & CS-A-210 088 (M. Libich) Apr. 30, 1982.

Chemical Abstracts, vol. 110, No. 17, Apr. 24, 1989, p. 402, Abstract No. 150957w, Columbus, Ohio US; & CS-A-248 241 (J. Bulik et al.) Jul. 15, 1988.

Chemical Abstracts, vol. 112, No. 17, Apr. 23, 1990, p. 383, Abstract No. 154847z, Columbus, Ohio, US; CS-A-261 849 (T. Kohlmayerova et al.) May 15, 1989. Ser. No. 526,917.

*Primary Examiner*—Howard E. Schain
*Attorney, Agent, or Firm*—Sughrue, Mion, Zinn, Macpeak & Seas

[57] ABSTRACT

A method of purifying human serum albumin which comprises subjecting human serum albumin-containing solution to heat treatment of about 50°–70° C. for 1–5 hours in the presence of acetyltryptophan and/or an organic carboxylic acid with 6–12 carbon atoms or a salt thereof.

10 Claims, No Drawings

METHOD OF PURIFYING HUMAN SERUM ALBUMIN USING ORGANIC CARBOXYLIC ACIDS AND ACETYL TRYPTOPHAN

FIELD OF THE INVENTION

This invention relates to a method of purifying human serum albumin and preferably genetically engineered human serum albumin.

BACKGROUND OF THE INVENTION

Albumin, in particular human serum albumin (hereinafter referred to as "HSA"), is a principal proteinaceous constituent of the blood. The protein is produced in the liver and is responsible for the maintenance of normal osmotic pressure in the circulatory system. HSA also functions as a carrier for various serum molecules.

HSA is used under various clinical circumstances. For example, patients in shock or with serious burns generally require repeated administration of HSA to restore and maintain blood volume thereby alleviating several trauma-associated symptoms. Patients with hypoproteinemia or fetal erythroblastosis may sometimes require treatment with HSA.

Thus, in conditions in which fluid loss occurs, such as in the case of surgical operation, shock, burn or edema-inducing hypoproteinemia, HSA administration finds a beneficial utility.

At present HSA is produced in the main as a product of fractionation of the blood collected from donors. However, this production method is disadvantageous in that it is uneconomical and an ample supply of blood is often difficult to procure. Furthermore, there is the ever present risk of contamination with infectious agents as hepatitis virus. It will therefore be useful to develop a substitute means of obtaining HSA.

The advent of recombinant DNA technology has made it possible to produce a variety of useful polypeptides in microorganisms. Thus, a number of mammalian polypeptides are produced in prokaryotes, for example human growth hormone, interferons, vaccines, hormones, enzymes and antibodies.

To overcome some of the above-mentioned difficulties in the production of HSA, processes are being established for the large-quantity production of HSA by genetic engineering techniques and for the high-level purification of genetically engineered HSA. Some methods are known for the production of HSA by utilizing recombinant DNA technology with yeast as host organisms (EP-A-123544, EP-A-248637 and EP-A-251744).

However, in producing HSA and in purifying the same from genetically engineered microorganisms, the crude HSA-containing materials are necessarily contaminated by microbial components, in the main microbial proteins. These contaminants have not been removed to a satisfactory extent by those methods which are used for the preparation of plasma-derived HSA.

SUMMARY OF THE INVENTION

An object of the present invention is to provide a method of efficiently purifying HSA produced intracellularly or extracellularly by genetically engineered microorganisms. The object is attained by subjecting the HSA-containing culture supernatant obtained by cultivating a genetically engineered and HSA-producing host, to heat treatment at pH 6-10 at about 50°-70° C. for about 1-5 hours in the presence of acetyltryptophan, or an organic carboxylic acid containing 6-12 carbon atoms or a salt thereof.

DETAILED DESCRIPTION OF THE INVENTION

The present invention can be applied to any HSA species prepared through the use of the recombinant DNA technology, without any particular limitation. Thus, for example, the invention may be practiced by using fractions that are obtained from culture supernatants derived either directly from genetically engineered, HSA-expressing cells (e.g. *Escherichia coli*, yeasts, *Bacillus subtilis*, animal cells, etc.) in the case of extracellular expression (secretory expression) or, in the case of intracellular expression, following a known cell lysis treatment process or processes involving, for example, freezing and thawing, glass bead treatment, application of high pressure, sonication, and/or enzyme treatment, as well as those fractions that are derived from a partial purification using known techniques, such as fractionation technique, adsorption chromatography, affinity chromatography, gel filtration, density gradient centrifugation and dialysis. By way of a non-limiting example, described herein below is a method of preparing an HSA-producing yeast strain. A method of obtaining an HSA gene-containing plasmid and transformation of yeast using the same are presented in the examples.

More specifically, said plasmid contains the HSA gene, a promoter, a signal sequence, a terminater and so forth. The albumin-encoding region contained in the plasmid is particularly a DNA sequence identical or substantially homologous to the HSA gene sequence, which can be obtained, for example from an optionally selected human cell line capable of producing HSA. Said DNA is a chromosomal DNA or a cDNA (complementary DNA). The chromosomal DNA can be separated from an HSA gene-containing genomic library and the HSA cDNA can be prepared in the conventional manner via the mRNA route.

The promoter is preferably derived from the host cell genomic DNA, in the hereinbelow example from *Saccharomyces cerevisiae*. The use of a high expression yeast gene promoter is preferred for the expression of HSA. Suitable promoter sequences include those that regulate the TRPI gene, ADHI or ADHII gene, acid phosphatase (PH03 or PH05) gene, isocytochrome C gene, a galactose metabolizing system (GAL1, GAL10 or GAL7), the invertase gene (SUC2), a gene coding for a glycolytic system enzyme, such as the enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triphosphate isomerase, phosphoglucose isomerase or glucokinase gene promoter, or the yeast conjugation pheromone gene coding the a-factor or α-factor.

In a further preferred mode of gene manipulation, a signal sequence is incorporated into the construct plasmid. It is preferred that the signal sequence be a host endogenous sequence. Thus in the example below, the signal sequence is yeast-derived. Preferred yeast signal sequences include those associated with the invertase and α-factor genes as in the signal sequence for HSA. A synthesized signal sequence for secretory expression cloned sequences in yeasts (U.S. patent application Ser. Nos. 190,553 and 311,556 corresponding to EP-A-

319641 and EP-A-329127, respectively) can be used as well.

As a result of introduction of this signal sequence, the HSA gene expression product enters the secretory pathway and is transported to the periplasmic space. Ultimately, secretion through the cell membrane into the culture medium occurs. Because cells need not be disrupted, the recovery step can be simplified and a considerable increase of yield can be obtained.

The plasmid further contains an appropriate terminator for the termination of transcription, in yeast for example the PH05 or GAP-DH terminator.

In the practice of the invention, yeasts, in particular strains of the genus Saccharomyces or Pichia, are preferable as the host. Among them, auxotrophic strains and antibiotic-sensitive strains are preferred. The G418-sensitive strain *Saccharomyces cerevisiae* AH 22 (a, his4, leu2, can1) and the like are particularly preferred.

The method of transformation includes, among others, the direct introduction of the plasmid into host cells and the integration of the plasmid into a yeast genome, for example by calcium phosphate microcoprecipitation, polyethylene glycol treatment of protoplasts or electroporation. The latter method is performed, for example, in the manner described below.

An HSA-producing yeast strain with the plasmid integrated in the yeast genome is used preferably in the practice of the invention. The plasmid contains a DNA sequence of part of a gene occurring naturally in the host yeast genome. The homologous sequence enhances the likelihood of the whole plasmid or a linear fragment thereof integrating stably into the host genome. This modification enables the culture of cells stably retaining the introduced genetic material in the absence of a selective pressure.

Usable as the sequence homologous to a host yeast chromosomal sequence are, in particular, amino acid-synthesizing or nucleic acid-synthesizing genes, ribosomal DNAs, the Ty factor, and the like. In a preferred embodiment, the host yeast is an amino acid-requiring or nucleic acid-requiring strain, namely a strain deficient in an amino acid-synthesizing or nucleic acid-synthesizing system gene. In that case, the cloned transfected amino acid-synthesizing or nucleic acid-synthesizing system gene serves to cure the mutation in the host and therefore can be used as a marker for transformant selection. As amino acid-synthesizing or nucleic acid-synthesizing system genes rendering an auxotrophic host yeast prototrophic, the artisan may consider, for instance, LEU2, HIS4, TRP1 and URA3.

More conventional hosts also can be used. For example, antibiotic resistance expression genes such as those providing resistance to cycloheximide, G418, chloramphenicol, bleomycin, hygromycin and other antibiotics, can be used in cases where the host is an antibiotic-sensitive strain.

The plasmid is incapable of autonomous replication in host yeasts. It is substantially free of a region for autonomous replication initiation in host yeasts, for example the origin of replication or an autonomously replicating sequence (ARS).

The plasmid may contain an origin of replication and one or more selective markers, each capable of functioning in bacterial hosts, in particular *Escherichia coli*, in addition to the above-mentioned promoter, HSA-encoding region and region homologous to a yeast genomic sequence. Useful features lie in the use of such origin of replication to function in *Escherichia coli* and one or more selective markers for *Escherichia coli* in the yeast hybrid vector. Thus, hybrid vector DNA can be obtained in large amounts by multiplication of and replication in *Escherichia coli*. For example, pBR322 contains an origin of replication to act in *Escherichia coli* and one or more selective markers for *Escherichia coli* which provide resistance to antibiotics, such as tetracycline and ampicillin, and is used advantageously as a part of the yeast hybrid vector.

The plasmid thus contains a promoter, the HSA-encoding region regulated by said promoter, a sequence following the coding region for terminating transcription and a sequence homologous to a host yeast genomic sequence. As desired, the plasmid may further contain a signal sequence for the secretory production, one or more selective markers for yeasts, an origin of replication to serve in *Escherichia coli*, and one or more selective markers for *Escherichia coli*. The plasmid is substantially free of an origin of replication to serve in yeasts. In the following, a method is described of preparing an appropriate recombinant using the plasmid mentioned above in a method for producing albumin.

It is desirable that the plasmid be cleavable at a site in the sequence that is homologous to the host yeast cell genome by restriction enzyme treatment. Linearization of the plasmid enhances integration into the region on the host yeast cell genome that is homologous to the plasmid. The linearized plasmid is integrated into the host chromosome with increased frequency as compared with a circular plasmid. The host yeast is preferably a mutant that will be rendered normal by the selective marker that is borne by the plasmid for insertion. An example of such a yeast mutant is *Saccharomyces cerevisiae* AH22 (a, his4, leu2, can1), which is leucine-requiring and histidine-requiring and is sensitive to the antibiotic G418.

Transformation of host yeast cells is performed by a known method, for example by polyethylene glycol treatment of protoplasts or by electroporation.

Whether the plasmid has been integrated into the genome and whether the gene introduced is stable are then determined. Specifically, integration at the expected locus can be confirmed by Southern blotting using as a probe the host yeast cell chromosomal sequence used for transformation. The stability of the albumin-encoding gene can be confirmed by establishing that albumin production and maintenance of prototrophism are maintained after subculturing of the transformant in non-selective medium.

A strain that has passed the above confirmation tests is likely to be a transformant carrying the HSA-encoding region in the desired locus of the host yeast cell genome. The transformant can be used again as the host for transformation with a second plasmid containing a HSA-encoding region. In this case, the region of the plasmid carrying yeast genomic sequences is homologous to a gene other than used in the first transformation.

Other host yeast cell genomic sequence that are suitable include the ribosome DNA and Ty factor (transposon of yeast element) which are present in multiple copies in each genome. Therefore, it would be possible to integrate the desired gene into the host genome at a plurality of loci by one transformation procedure.

In the following, a suitable method of integration is given by way of example, which is however by no means limitative of the scope of the invention.

The host is *Saccharomyces cerevisiae* AH22 (hereinafter AH22), which is leucine-requiring, histidine-requiring and G418-sensitive (with mutations in the leucine-synthesizing system gene LEU2 and the histidine-synthesizing system gene HIS4). AH22 is transformed with an HSA gene-containing plasmid having the LEU2 gene as the sequence homologous to the host yeast cell genomic DNA. The thus-obtained transformant carries the plasmid containing the albumin-encoding gene as an insert in the LEU2 gene sequence situated in the yeast genome resulting in a non-leucine-requiring strain, hence can grow in a leucine-free medium.

Then the transformant is used as the host and is transformed with a second plasmid having the HIS4 gene rendering the host non-histidine requiring as the sequence homologous to the host yeast cell genome and containing the region coding for albumin. The thus-obtained transformant is a non-histidine-requiring strain capable of growing in a histidine-free medium with the plasmid containing the albumin-encoding region inserted in the HIS4 gene sequence situated in the yeast genome. At this point of time, the desired gene for expression, namely the albumin gene, has been introduced at two sites, namely in LEU2 and HIS4.

The transformant, which is now neither leucine-requiring nor histidine-requiring, is used as the host and transformed with a plasmid having TRP1 as the sequence homologous to the host yeast cell chromosomal sequence. This plasmid contains not only the albumin-encoding region but also the G418 resistance gene. The transformant obtained carries the plasmid containing the albumin-encoding region and G418 resistance gene as inserted in the TRP1 gene sequence situated in the yeast genome and shows resistance to the antibiotic G418. This transformant therefore contains the albumin gene at a total of three sites, namely in the LEU2, HIS4 and TRP1 gene loci in the yeast genome. In this case, the order of insertion is not particularly critical.

If a mutant requiring a number of nutrients and showing resistance to a number of antibiotics can be obtained, it will be possible to introduce a useful gene at a plurality of regions in the host genome. Integration of a plurality of genes makes it possible to produce the desired product in large amounts.

The transformant is cultivated in a known medium, for example YPD liquid medium [1% yeast extract (Difco), 2% Bactopolypeptone (Difco), 2% glucose]. Cultivation is generally carried out at a temperature of 15°–43° C. (optimally about 30° C.) for about 20–100 hours, if necessary with aeration and/or agitation.

The cells are separated and the thus-obtained culture supernatant containing HSA is subjected to the following purification procedure. (a) Heat treatment This step results in the inactivation of contaminant proteases.

As an additive during the heat treatment, acetyltryptophan and/or an organic carboxylic acid containing 6–12 carbon atoms or a salt thereof may be used. Acetyltryptophan is used at a concentration of about 1 to 100 mM, preferably 1 to 10 mM. Examples of the organic carboxylic acid with 6–12 carbon atoms include caproic acid (C6), caprylic acid (C8), capric acid (C10) and lauric acid (C12), among others, with caprylic acid being preferred. The salt of said acids includes alkali metal salts (e.g., sodium and potassium salt), and alkaline earth metal salts (e.g., calcium). The organic carboxylic acid with 6–12 carbon atoms or a salt thereof is used in an amount of about 1–100 mM, preferably 1–10 mM.

The heat treatment is conducted, for example, at pH 6–10 and at about 50°–70° C. for about 1–5 hours. (b) After-treatment The HSA can be further purified using a known technique, for example, fractionation, ultrafiltration, gel filtration, ion exchange chromatography or affinity chromatography.

HSA-containing pharmaceutical compositions and dosage forms can be prepared by using known pharmaceutical preparation techniques.

EXAMPLE 1

*Saccharomyces cerevisiae* (pYN026/AH22 #6) capable of producing HSA was cultured. The supernatant was divided into three portions, A, B and C. To the two portions, A and B, were added 5 mM acetyltryptophan and 5 mM sodium caprylate, and one portion, B was heated at 60° C. for 3 hours. The portion heated was then cooled. The three portions were concentrated, were adjusted to pH 4.0, were allowed to stand at room temperature for 24 hours and then were subjected to gel filtration analysis. Namely, each sample solution (50 μl) was injected into a TSK gel G3000 SW$_{xL}$ column equilibrated in advance with 0.05M acetate buffer (pH 6.7) containing 0.3M NaCl Elution was carried out using the above-mentioned buffer at a flow rate of 0.5 ml/min. HSA was detected by measuring A$_{280}$ and the HSA content of each sample was determined based on the height of the A$_{280}$ peak. The results are shown in Table I.

TABLE I

| Sample | Percent degradation* |
|---|---|
| (A) Supernatant before heating | 0 |
| (B) Supernatant after heating | 0 |
| (C) Unheated control supernatant | 55.2 |

*[(Area of components of molecular weight lower than that of HSA)/(Area of intact HSA + area of components of molecular weight lower than that of HSA)) − (Area of components of molecular weight lower than that of HSA/(Area of intact HSA + area of components of molecular weight lower than that of HSA (of treated, unheated sample, e.g., portion A above)) × 100].

Reference Example

Preparation of HSA-producing yeast

1. Plasmid

The plasmid used for secretory expression of mature human serum albumin (HSA) was pYN026. pYN026 is an 11.2 kb *Escherichia coli*/yeast shuttle vector comprising the GAL1 promoter, a modified signal sequence for HSA (as described below), a cDNA for HSA and the PH05 terminator in that order and further containing the genes for the expression of Amp (ampicillin) resistance and Km (kanamycin) resistance in *Escherichia coli*, of G-418 resistance in yeasts and the LEU2 gene which will complement the LEU2 mutation. Each of the above-mentioned regions and genes was prepared by the methods described in the following literature or modifications thereof or was purchased from the following commercial sources.

GAL1 promoter and HSA cDNA: U.S. patent application Ser. No. 311,556 or EP-A-329127

PH05 terminator: U.S patent application Ser. No. 296,868 or EP-A-216573

G418 resistance gene: Oka, A., Sugisaki, H. and Takanami, M., J. Mol. Biol., 147, 217 (1981); Jimenez, A. and Davies, J., Nature, 287, 869 (1980); U.S. patent application Ser. No. 612,796 or EP-A-163491;

LEU2: derived from the plasmid pBT1-1 (commercially available from Boehringer-Mannheim);

*Escherichia coli* replication origin region and ampicillin resistnace gene: derived from the plasmid pUC19 (commercially available from Takara Shuzo) and pAT153 (commercially available from Amersham Co.).

The construction of the plasmid was carried out using the conventional methods described in "Molecular Cloning", Cold Spring Harbor Laboratory (1982).

A HSA/SUC2 hybrid signal peptide was derived from the HSA signal peptide by replacing the −5 to −1 amino acid sequence with the −5 to −1 amino acid sequence of the SUC2 signal peptide and further replacing the −3 amino acid with Val resulting in the following sequence:

$$\underset{\text{MetLysTrpValThrPheIleSerLeuLeuPheLeuPhe}\underline{\text{AlaLysValSerAla}}}{-18 \qquad -15 \qquad -10 \qquad -5 \qquad -1}$$

2. Introduction of the plasmid into yeast

The plasmid for secretory expression of human serum albumin was introduced into the yeast *Saccharomyces cerevisiae* AH22 (Proc. Natl. Acad. Sci. USA, 75, 1929–1933 (1978)) in the following manner.

*Saccharomyces cerevisiae* AH22 was cultured overnight with shaking at 30° C. in 50 ml of YPD medium (YPD was prepared by dissolving 10 g of yeast extract and 20 g of Bacto-peptone in water to make 900 ml. The solution was autoclaved and when cooled mixed with 100 ml of separately autoclaved 20% glucose). The culture was centrifuged, cells thus obtained were suspended in 20 ml of water and the suspension was again centrifuged. The cells thus obtained were suspended in 10 ml of a solution containing 50 mM dithiothreitol, 1.2 M sorbitol and 25 mM EDTA, pH 8.5, and the suspension was shakened gently at 30° C. for 10 minutes. Cells were recovered by centrifugation and suspended in 10 ml of 1.2 M sorbitol. Again cells were collected by centrifugation and suspended in 10 ml of 1.2M sorbitol.

The cells were collected by centrifugation and suspended in 10 ml of a solution containing 0.2 mg/ml Zymolyase 100T (Seikagaku Corporation), 1.2M sorbitol, 10 mM EDTA and 0.1M sodium citrate, pH 5.8. The suspension was shakened gently at 30° C. for 1 hour. Cells were recovered by centrifugation, washed with 10 ml of 1.2 M sorbitol and then with 10 ml of 10 mM calcium chloride plus 1.2 M sorbitol. Cells collected by centrifugation were suspended in 10 ml of 10 mM calcium chloride plus 1.2M sorbitol.

A 100-μl portion of the suspension was placed into a sterilized test tube and mixed with 5 μg of the plasmid. The mixture was allowed to stand at room temperature for 15 minutes. To the mixture was added 1.2 ml of a solution of 20% polyethylene glycol 4000, 10 mM calcium chloride and 10 mM Tris-hydrochloride, pH 7.5. After gentle shaking, the resultant mixture was allowed to stand at room temperature for 20 minutes. Cells were collected by centrifugation and suspended in 0.1 ml of YPD medium containing 1.2M sorbitol and 10 mM calcium chloride and the suspension was shakened gently at 30° C. for 30 minutes.

A 1, 5, 10, 20 and 50 microliter portion of the suspension was added individually to 10 ml of a solution maintained at 45° C. and containing 1.2M sorbitol, 3% noble agar, 2% glucose and 0.7% yeast nitrogen base (Difco) and the resultant suspension was spread on individual plates comprising 1.2M sorbitol, 3% Bacto-agar, 2% glucose and 0.7% yeast nitrogen base. After solidification of the plates, the stationary cultures was maintained at 30° C. for 3 days. Each colony that formed was collected with a toothpick, suspended in 3 ml of 0.7% yeast nitrogen base plus 2% glucose, and shake-cultured at 30° C. for 2 days. A 1.5-ml portion of the culture was centrifuged and the cells collected were suspended in 3 ml of YPG medium (YPG was prepared by dissolving 10 g of yeast extract and 20 g of Bacto-peptone in water to make 900 ml. The solution was autoclaved and when cooled mixed with 100 ml of separately autoclaved 20% galactose) and shake-cultured at 30° C.

3. Cultivation of yeast for the expression of human serum albumin

The yeast *Saccharomyces cerevisiae* AH22 transformed and capable of secretory expression of human serum albumin was cultivated in the following manner. A loopful of the above-mentioned recombinant yeast grown on a plate comprising 0.7% yeast nitrogen base, 2% glucose and 3% Bacto-agar was inoculated into 50 ml of YNB medium (0.7% yeast nitrogen base and 2% glucose) and cultured at 30° C. for 2 days. The whole culture was then inoculated into 500 ml of YNB medium and cultivated at 30° C. for 2 days. Cells were collected by centrifugation, suspended in 500 ml of YPG medium and shake-cultured at 30° C.

EXAMPLE 2

Material

Pichia pastoris-derived r-HSA (recombinant HSA) solution was obtianed in a manner similar to that described in Example 1. The final preparation was found to contain about 4 mg/ml of r-HSA (assayed by HPLC).

Methods

I. Gel filtration analysis by HPLC

A sample of r-HSA-containing solution (50 μl) was injected into a TSK gel G3000 SW$_{XL}$ column equilibrated in advance with 50 mM sodium phosphate buffer (pH 6.5) containing 0.1% sodium azide and 0.3% sodium chloride. Elution was carried out using, the above-mentioned buffer at a flow rate of 0.5 ml/min. The elution of r-HSA was detected by measuring $A_{280}$ and plotted against elution time and the r-HSA content of each sample was determined based on the height of the $A_{280}$ peak.

II. Heat treatment at various pH levels

N-acetyl-D,L-tryptophan and caprylic acid were added to the Pichia yeast-derived r-HSA solution, each to a concentration of 1 mM. After dissolution, the resultant solution was distributed in 10 ml portions into 6 tubes. The pH of the solution in each tube was adjusted to 5.0, 6.0, 7.0, 8.0, 9.0 or 10.0 by adding 0.1N NaOH or HCl. Each tube was incubated at 65° C. for 3 hours and then cooled at room temperature. The tubes were centrifuged at 2,000 × g for 15 minutes and the supernatant of each was used as a sample for gel filtration analysis by HPLC as described above under section I.

Table II summarizes the results obtained in the above manner in terms of r-HSA recovery percentage after heat treatment, elimination of r-HSA degradation products (determined based on the height of the $A_{280}$ peak of components of molecular weight lower than that of HSA), and coloration ratio (350 nm/280 nm).

TABLE II

Effect of pH on heat treatment of r-HSA solution

| pH | Recovery (%) | | $A_{350}/A_{280}$ |
|---|---|---|---|
| | r-HSA | Degraded r-HSA | |
| Before heat treatment | 100 | 100 | 0.175 |
| 5.0 | 55 | 34 | 0.217 |
| 6.0 | 97 | 62 | 0.207 |
| 7.0 | 102 | 57 | 0.209 |
| 8.0 | 98 | 34 | 0.238 |
| 9.0 | 94 | n.d.[1] | 0.268 |
| 10.0 | 108 | n.d. | 0.288 |

[1]Not detected as a peak in HPLC analysis.

The recovery of r-HSA at pH 5.0 was as low as 55%. At pH 6.0–10.0, the recovery was nearly 100%. At pH 5.0, turbidity was confirmed after heat treatment, which was not observed at other pH levels, centrifugation yielded a considerable amount of sediment.

The extent of elimination of r-HSA degradation products increased satisfactorily with the increase of pH from 6.0 to 8.0. At pH 9.0 or higher, no degradation product peak was observed in HPLC.

The 350 nm/280 nm absorbance ratio, which is an index to the degree of coloration of r-HSA, increased upon heat treatment at all pH levels, showing a tendency toward progressive increase with the pH increase from 6.0 to 10.0.

While the invention has been described in detail and with reference to specific examples thereof, it will be apparent to one skilled in the art that various changes and modifications can be made therein without departing from the spirit and scope thereof.

What is claimed is:

1. A method of purifying human serum albumin which comprises the steps of:
    (a) treating a human serum albumin-containing solution obtained from the culture supernatant of or lysate of recombinantly engineered cells, with acetyltryptophan at a concentration of about 1–100 mM and an organic composition acid or salt thereof of 6–12 atoms at a concentration of about 1–100 mM;
    (b) adjusting the pH of said solution to about 6–10;
    (c) heating said solution of step (b) at a temperature of about 50°–70° C. for about 1–5 hours; and
    (d) separating the human serum albumin from said solution of step (c).
2. The method of claim 1 wherein said cells are of a prokaryote.
3. The method of claim 1 wherein said cells are of a eukaryote.
4. The method of claim 3 wherein said eukaryote is a yeast.
5. The method of claim 4 wherein said yeast is *Saccharomyces cerevisiae*.
6. The method of claim 1 wherein said carboxylic acid is selected from the group consisting of caproix acid, caprylic acid, capric acid and laruic acid.
7. The method of claim 1 wherein the concentration of said carboxylic acid salt is 1–100 mM.
8. The method of claim 7 wherein said carboxylic acid salt is comprised of 6–12 carbon atoms.
9. The method of claim 7 wherein said carboxylic acid salt is comprised of an alkali metal salt or earth metal salt.
10. The method of claim 1 wherein the alkaline pH of said solution is at 6–10.

* * * * *